United States Patent [19]

Kageyama et al.

[11] Patent Number: 5,610,045
[45] Date of Patent: Mar. 11, 1997

[54] PRODUCING A HIGH CONTENT OF ACETATE KINASE USING *BACILLUS STEAROTHERMOPHILUS*

[75] Inventors: Masao Kageyama, Kyoto; Toyohiko Suga, Osaka; Kenzo Motosugi; Hiroshi Nakajima, both of Kyoto, all of Japan

[73] Assignee: Unitika Ltd., Hyogo, Japan

[21] Appl. No.: 458,770

[22] Filed: Jun. 2, 1995

Related U.S. Application Data

[63] Continuation of Ser. No. 931,507, Aug. 21, 1992, abandoned, which is a continuation of Ser. No. 604,392, Oct. 26, 1990, abandoned, which is a continuation of Ser. No. 789,934, Oct. 22, 1985, abandoned, which is a continuation of Ser. No. 152,957, May 23, 1980, abandoned.

[30] Foreign Application Priority Data

May 23, 1979 [JP] Japan .................................. 54-64301

[51] Int. Cl.$^6$ .............................. C21N 9/12; C21N 1/20
[52] U.S. Cl. ................. 435/194; 435/252.1; 435/252.5
[58] Field of Search ............................ 435/194, 252.1, 435/252.5

[56] References Cited

FOREIGN PATENT DOCUMENTS 0025088  2/1977  Japan .................................. 435/194

OTHER PUBLICATIONS

Purification and Properties of Acetate Kinase from *Bacillus Stearothermophilus*, *J. Biochem*, vol. 84, 1978, pp. 193–203, Nakajima et al.
Industrial Applications of Microbiology, John Wiley & Sons 1977 pp. 72–77.

*Primary Examiner*—Michael G. Wityshyn
*Assistant Examiner*—Blaine Lankford
*Attorney, Agent, or Firm*—Sughrue, Mion, Zinn, Macpeak & Seas

[57] ABSTRACT

A process is described for cultivating thermophilic bacteria of the genus Bacillus having the ability to produce acetate kinase, wherein said cultivation is carried out continuously at a dilution rate (D) in the range from about $0.9\ \mu_{max}$ to $1.0\ \mu_{max}$, wherein D is the dilution rate (1/hr), and $\mu_{max}$ is the maximum specific growth rate (1/hr), to thereby produce bacterial cells having a high content of acetate kinase.

11 Claims, No Drawings

PRODUCING A HIGH CONTENT OF ACETATE KINASE USING *BACILLUS STEAROTHERMOPHILUS*

This is a Continuation of Application Ser. No. 07/931, 507 filed Aug. 21, 1992 which is a File Wrapper Continuation of 07/604,392 filed Oct. 26, 1990 which is a File Wraper Continuation of 06/789,934 filed Oct. 22, 1985 which is a File Wrapper Continuation of 06/152,957 filed May 23, 1980 all now abandoned.

BACKGROUND OF THE INVENTION

1. Field of the Invention

This invention relates to a process for producing bacterial cells having a high content of acetate kinase. More specifically, it relates to a process for producing bacterial cells having a high content of acetate kinase per gram of dry cells, which comprises continuously cultivating thermophilic bacteria of the genus Bacillus under specified conditions.

2. Description of the Prior Art

In recent years, the utilization of enzymes as biochemical catalysts in areas not previously considered has been investigated in view of their often superior properties, such as (1) high specificity, (2) usefulness under mild reaction conditions, (3) energy conservation, and (4) freedom from pollution.

The trend of investigations of enzymes in the biochemical industry has shifted away from the earlier almost exclusive interest in hydrolases, and has more recently been directed to finding a way to reproduce energy sources for good efficiency and to utilize the advantages of enzymes in synthesizing compounds which are difficult to produce by chemical processes. To realize this, a so-called bioreactor has been developed. The bioreactor consists of a main reactor for producing substances, and a sub-reactor for supplying energy to the main reactor. The enzymes for use in the sub-reactor need to reproduce adenosine triphosphate (to be abbreviated ATP), which is a source of energy for living organisms, and the use of enzymes generically called phosphotransferases has been considered, and methods involving the use of phosphotransferases are known. For example, one method suggested comprises using glycerokinase (*Journal of Applied Bacteriology*, Vol. 38, pp. 301–304, 1975); a second method comprising the use of acetate kinase is described in Japanese Patent Application (OPI) No. 25088/77 (the term "OPI" as used herein refers to a "published unexamined Japanese patent application"); and a third method comprising the use of pyruvate kinase is described in Japanese Patent Application (OPI) No. 9392/78. Of these, the method using acetate kinase is considered to be most suitable because the equilibrium constant of the reaction during the production of ATP is very advantageous with respect to the production of ATP, and the acetylphosphoric acid source material required for the production of ATP by this enzyme is industrially available at low cost (*American Institute of Chemical Engineers Journal*, Vol. 22, p. 1079).

Since acetate kinase is an endobacterial enzyme, it is generally prepared by a method which comprises destroying the bacterial cells and extracting the enzyme from the resulting supernatant liquid. The supernatant liquid also contains various other substances derived from the bacterial cells, and it is extremely difficult to separate and purify the desired enzyme. For example, as described in *Journal of Biochemistry*, Vol. 84, No. 1, 195–203, 1978, acetate kinase can be purified by a complex process which involves destroying the bacterial cells, removing nucleic acids using Streptomycin, salting out the resulting supernatant liquid with ammonium sulfate, and subjecting the resulting crude enzyme precipitate to complex steps such as chromatography on a DEAE (Diethylaminoethyl) cellulose column, chromatography on a hydroxyappatite column, chromatography on an ultrogel column, and chromatography on a DEAE Sephadex column. Another complex method for purifying acetate kinase is described in *Methods in Enzymology*, Vol. I, pp. 591–595, including the steps of grinding up the bacterial cells and subjecting them to a combination of two acetone fractionations and three salting out steps with ammonium sulfate.

Because these methods are complex and timeconsuming, the cost of production of acetate kinase per unit of enzyme is very high, and this constitutes a serious obstacle to the industrial development of bioreactors.

Another problem in the production of acetate kinase is the low productivity of bacterial cells. Since acetate kinase is an endobacterial enzyme, the productivity would be increased generally by adding successively further nutrient sources to a fermentor tank in which cultivation is carried out by a batchwise method or by increasing the coefficient of oxygen transfer capacity by pressurizing the tank and/or passing oxygen, to thereby increase the amount of the bacterial cells. However, using such a cultivating method it is difficult to cause the logarithmic growth phase to continue, and so it becomes desirable to harvest cells which are about to shift to the stationary phase. Consequently, the content of the desired endobacterial enzyme is reduced, or a longer period of time is required for the cultivation. Furthermore, the cost of product is also increased, because of the increased consumption of the culture medium and oxygen. Thus, typically, although the amount of the cells that can finally be produced is increased, the amount of the desired cells per unit of time and per unit of cost of cultivation, and the productivity with respect to the enzyme, actually decreases. In fact, when these conventionally known techniques are applied to bacteria having the ability to produce acetate kinase, the content of acetate kinase in the bacterial cells is much smaller than that of bacterial cells which are cultivated by a batch process with reduced productivity of the cells and harvested during the logarithmic growth phase thereof.

Generally, enzymes participating in an energy metabolism system, such as glycerokinase or acetate kinase, are called constituent enzymes, and are known to be produced within bacterial cells irrespective of the cultivation conditions. For example, an article in the *Journal of Applied Bacteriology*, Vol. 38, pp. 301–304 (1975) stated that the productions of the rhodanase and glycerokinase as an endobacterial enzyme were investigated using a continuous cultivation method, and that the content of the enzyme per unit cell is dependent on the type of carbon sources in the nutrient medium, but is not affected by the dilution rate. An article in the *Journal of Bacteriology*, Vol. 133, No. 2, pp. 992–1001 (1978) stated that the relation between the content of acetate kinase per unit cells of *Escherichia coli* and its specific growth rate was investigated in a continuous cultivation method, and that no correlation was noted between the content of acetate kinase per unit cells and the specific growth rate. Furthermore, it is stated in *Journal of Applied Chemistry and Biotechnology*, Vol. 26, pp. 324–325 (1976) that the production of α-amylase by *Bacillus stearothermophilus* was investigated, and that the production of α-amylase as an exobacterial enzyme is proportional to the amount of bacterial cells. However, it is not described in the above *Journal of Applied Chemistry* that the productivity of α-amylase per unit cells is increased.

SUMMARY OF THE INVENTION

It is an object of this invention to provide a process for obtaining acetate kinase with good efficiency by producing bacterial cells having a high content of acetate kinase.

After extensive investigations in order to achieve the aforesaid object, it has surprisingly been found that when continuous cultivation is carried out while controlling the dilution rate within a specified range, bacterial cells having a higher content of acetate kinase per unit cells than the maximum content of acetate kinase per unit cells in bacterial cells obtained by a batch process can be obtained; furthermore, the productivity of bacterial cells is simultaneously increased.

Thus, the present invention provides a process for cultivating a thermophilic bacterium of the genus Bacillus having the ability to produce acetate kinase, wherein said cultivation is carried out continuously at a dilution rate (D) in the range from about 0.9 $\mu_{max}$ to 1.0 $\mu_{max}$, wherein D is the dilution rate (1/hr), and $\mu_{max}$ is the maximum specific growth rate (1/hr) of said bacterium under the continuous cultivation conditions, to thereby produce bacterial cells having a high content of acetate kinase. The bacterial cells having a high content of acetate kinase in this invention is bacterial cells having a higher content of acetate kinase than the content of acetate kinase in bacterial cells obtained during the logarithmic growth period in the batchwise cultivation.

The bacterial cells cultivated and harvested by the process of the invention have a higher content of acetate kinase per unit cell than bacterial cells obtained by conventional batch processes, and the productivity of cells is high. Hence, acetate kinase can be obtained with good efficiency, and the cost of extraction and purification per unit weight of acetate kinase can be drastically reduced.

DETAILED DESCRIPTION OF THE INVENTION

Any bacteria of the genus Bacillus capable of producing heat-resistant acetate kinase can be used as the thermophilic bacteria of the genus Bacillus having the ability to produce acetate kinase in this invention. The heat-resistant acetate kinase in this invention is an acetate kinase wherein the maximum residual activity of the acetate kinase can be maintained at 90% or more based on the original activity, preferably 95% or more, most preferably 100% when measured by the following heat-resistant test. A heat-resistance test was carried out by treating the acetate kinase with a buffer solution at 50° C. for 15 minutes. The concentration and pH of the buffer solution are adjusted to a suitable rang, depending upon the type of acetate kinase produced. However, in general, the concentration and pH of the buffer solution are from 5 to 5 mM to 500 mM and from 2 to 11, respectively. The suitable concentration and pH for the acetate kinase illustrated in this invention are about 50 mM and 6.5 to 8.0, respectively, and the activity was measured according to the method as described in *J. Biol. Chem.*, Vol. 249, p. 2567 (1974). For example, *Bacillus stearothermophilus* can be cited as a preferred bacterium. Specific strains of *Bacillus stearothermophilus* that can be used in the process of the invention are those deposited as ATCC 7953, ATCC 8005, ATCC 10149, and NCA 1503. These strains are desirable because they grow fast and the content of acetate kinase per unit cells is high. Of these, ATCC 7953, ATCC 10149 and NCA 1503 are most commercially promising because they have good stability and other operating characteristics in continuous cultivation. These strains are available from the American Type Culture Collection, 12301 Parklawn Drive, Rockville, Md. 20852, U.S.A. ATCC 7953 was deposited in January, 1941. ATCC 8005 was deposited in March, 1941. ATCC 10149 was deposited in November, 1946. NCA 1503 was deposited in July, 1975.

In a nutrient medium used in cultivating bacteria in this invention, carbohydrates such as glucose, sucrose, fructose, starch hydrolyzate, molasses and sulfite pulp spent liquor, organic acids such as acetic acid and lactic acid, and also alcohols, oils and fats, fatty acids and glycerin which bacteria to be used can assimilate can be used as carbon sources. Examples of nitrogen sources that can be used in this nutrient medium include inorganic and organic materials, such as ammonium sulfate, ammonium chloride, ammonium phosphate, ammonia, amino acid, peptone, meat extract and yeast extract. Furthermore, inorganic salts of calcium, sodium, phosphoric acid, zinc, iron, magnesium, manganese, copper, calcium, and cobalt, and optionally traces of metal salts, corn steep liquor, vitamins, nucleic acids, etc., may also be used. Any general nutrient media for bacteria can be used in this invention.

The cultivation in accordance with this invention is preferably carried out under aerobic conditions with the concentration of dissolved oxygen being at least 0.5 ppm by weight. The cultivation temperature is from about 40° to 75° C., and is preferably from 48° to 61° C., because the bacterial strains used are thermophilic. The pH of the nutrient medium is maintained at from about 4.5 to 9.0, and is preferably from 6.8 to 8.0.

The dilution rate (abbreviated D) is defined by the following equation (I), viz., $$D = \frac{F}{V} \quad (I)$$

wherein,

D is the dilution rate (1/hr)

F is the speed at which the starting liquor is fed into a fermentor and is withdrawn therefrom (liter/hr) (the in flow and out flow is substantially identical), and V is the amount (liters) of the liquor in the fermentor.

The $\mu_{max}$ in this invention denotes the maximum specific growth rate (1/hr) of a bacterium under the cultivation conditions while in continuous cultivation. More particularly, it is the specific growth rate measured when, for a substance in continuous cultivation (chemostat; Herdert, Elsworth, Telling, *Journal of General Microbiology*, Vol. 14, No. 8, pp. 601–622, 1956), D is increased and the concentration of the cells can no longer be maintained at a steady value (i.e., at the time of "wash out" defined below). For example, the $\mu_{max}$ of a thermophilic bacterium in this invention can be determined by the following procedure: 1.5 to 20 liters of a nutrient medium is charged into a fermentor having a capacity of 2 to 30 liters, and while maintaining the medium at 40° to 75° C., and preferably 48° to 61° C., and a pH of 4.5 to 9.0, and preferably 6.0 to 8.0, the bacterium is inoculated and cultivated batchwise. When the bacterium begins to grow, and the concentration of carbon sources in the culture broth reaches not more than 0.01% by weight, a nutrient medium having the same composition as that charged into the fermentor initially is used, and continuous cultivation of the bacterium is started, using carbon sources as the only growth restricting factor. In this manner, a substance environmental-type continuous cultivation method (chemostat) can be preset. When the continuous cultivation reaches a steady state, D is increased stepwise, and the concentration of the bacterial cells in the fermentation broth and the amount of residual carbon sources are measured periodically. When D is gradually increased and exceeds the specific growth rate of the bacterium, the concentration of the bacterium maintained at a steady value begins to decrease, and, on the other hand, the concentration of the carbon sources begins to increase, and the steady state of continuous cultivation can no longer be maintained as the dilution rate D is further increased. This state is called "wash out", and the specific growth rate at the time of wash out is $\mu_{max}$.

The $\mu_{max}$ value for a given bacterium varies depending upon the type of the nutrient medium and the cultivation conditions, but remains at a certain fixed value if the combination of these factors does not change. Thus, once it is measured., it is reliable over a long period of time.

In the present invention, it is necessary that the continuous cultivation be carried out by adjusting D to at least 0.9 time $\mu_{max}$ of a bacterium used. The content of acetate kinase in bacterial cells obtained by performing continuous cultivation while adjusting D to at least 0.9 time $\mu_{max}$ of the bacterium used in this invention exceeds the maximum content of acetate kinase per unit cells of bacterial cells obtained by a batch process, and the productivity of the bacterial cells is increased. Particularly, when D is maintained close to $\mu_{max}$ the content of acetate kinase in the bacterial cells is 1.3 times as large as that of the cells obtained by a batch process. On the other hand, the content of acetate kinase in bacterial cells continuously cultivated at a D of less than 0.9 $\mu_{max}$ is lower than that of cells obtained by a batch process.

In the present invention, D can be controlled, after ordinary pre-cultivation and batchwise cultivation are performed to a desired cell concentration, by then switching to continuous cultivation. The time of controlling D may be any during the cultivation period. Desirably, the cultivation is switched over to continuous cultivation in the last stage of the logarithmic growth phase in the batchwise cultivation, and then immediately, D is adjusted to the desired value.

One embodiment of the invention is described below with reference to *Bacillus stearothermophilus* NCA 1503. When this strain is cultivated in a nutrient medium containing glucose as a carbon source at an optimal temperature (57° C.) and an optimal pH (6.8) in a 30-liter fermentor (charged with 20 liters of the culture medium) by a substance environmental-type continuous cultivation method. The $\mu_{max}$ value measured under these conditions 1.1 (1/hour). Accordingly, in order to perform continuous cultivation at D=$\mu_{max}$, a fresh nutrient medium of the same composition is continuously fed into the fermentor in an amount 1.1 times that charged into the fermentor per hour, i.e., at a rate of 22 liters/hr in view of equation (I), by means of a metering pump, and at the same time, the culture broth is withdrawn at the same rate from the fermentor.

Isolation of acetate kinase from the bacterial cells obtained by the process of this invention may be achieved by conventional procedures. For example, this can be done by crushing the cells, centrifuging them, adding an organic solvent or various salts to the resulting enzyme solution and fractionally purifying acetate kinase, or purifying it by adsorption onto a carrier. An example of such a method is described in the above-cited *Journal of Biochemistry*, Vol. 84, No. 1, pp. 193 to 203, 1978. When the properties of crystals obtained by purification in accordance with this method are examined by elemental analysis, absorbance in the ultraviolet region, the measurement of molecular weight, etc., they coincide totally with those of acetate kinase obtained by bacterial cells produced by a conventional batchwise process.

The bacterial cells cultivated and harvested by the present invention have a higher content of acetate kinase per unit cells than cells obtained by a batchwise process, and the productivity of the cells is also high. Thus, acetate kinase can be obtained with good efficiency, and the cost of extraction and purification per unit weight of acetate kinase can be drastically reduced. Furthermore, since the present invention is a continuous cultivation process and permits control of cultivation by control of D, it has the advantage that the cultivation can be easily controlled, and the cultivation conditions can be maintained automatically.

The following examples illustrate the present invention more specifically. In the examples, the content of acetate kinase was determined as follows: The enzyme activity of acetate kinase was measured by using a method which comprises converting changes in ATP into changes in nicotinamide adenine dinucleotide reduced type (to be referred to as NADH hereinbelow) and tracing them by absorbance at 340 nm (*Journal of Biological Chemistry*, Vol. 249, p. 2567, 1974), and the enzyme activity required to reduce the absorbance of 1 micromol of NADH at 340 nm per minute is defined as 1 unit (to be referred to as U). The productivity of acetate kinase is defined by the content of acetate kinase (U/g of dry cells)×the productivity of cells (g dry cells/liter/hr).

EXAMPLES 1 AND 2 AND COMPARATIVE EXAMPLES 1, 2 AND 3

Strain used:

*Bacillus stearothermophilus* ATCC 7953 Composition of a nutrient medium: containing glucose as a carbon source, and the following ingredients.

Glucose: 1.3 g $(NH_4)_2SO_4$: 1.0 g

Yeast extract (product of Oriental Yeast Co., Ltd.): 0.5 g $KH_2PO_4$: 0.5 g $Na_2HPO_4 12H_2O$: 0.5

$MgSO_4$: $7H_2O$: 0.1 g

Tap water: 1 liter to dissolve the above ingredients

Pre-cultivation

A 100 ml Erlenmeyer flask was charged with 20 ml of the nutrient medium of the above composition, and a 500 ml Erlenmeyer flask was charged with 100 ml of the same nutrient medium. Each of the flasks was closed up with a cotton stopper, and sterilized with pressurized steam at 121° C. and 1 kg/cm for 10 minutes. After cooling, 5 mg of lyophilized cells obtained from American Type Culture Collection were aseptically inoculated in the 100 m Erlenmeyer flask. Using a rotary shaker (a product of Takasaki Seisakusho), the cells were cultivated under rotation and shaking at 55° C. for about 24 hours at a speed of 160 rpm. The cells were seen to grow and the turbidity of the culture broth increased. The absorbance of the culture broth at 660 nm (measured by a 101 type spectrophotometer made by Hitachi Limited; referred to hereafter as $OD_{660}$ nm) reached 0.8 to 1.0. The culture broth obtained was then inoculated in an amount of about 5 ml in the 500 ml Erlenmeyer flask, and under the same conditions as above, the flask was rotated while shaking for several hours. The $OD_{660}$ nm reached about 1.0. The cultivation under rotation and shaking was stopped. The resulting product was us d as a pre-culture broth for the main cultivation.

Main cultivation

A 30-liter fermentor (MSJ-U type flat blade turbine type; a product of Marubishi Rika Sochi K. K.) was charged with 20 liters of a nutrient medium of the aforesaid composition, and sterilized with pressurized steam at 121° C. and 1 kg/cm² for 15 minutes. After presetting the cultivation temperature at 57°±1° C., the pH at 6.5 to 7.0 (adjusted with 4N-NaOH), the air flow rate at 20 liters/rain, and the stirring speed at 900 rpm, about 1 liter of the preculture broth was inoculated, and batchwise cultivation was started. Since foams occur during the cultivation, a small amount of an anti-foamer (KM-70, a product of Shinetsu Chemical Co., Ltd.) was added. The growth of the cells was traced by $OD_{660\ nm}$. Logarithmic growth occurred, and in about 2.5 hours, $OD_{660\ nm}$ reached 1.0. Glucose in the culture broth was almost completely consumed (measured by the Somogyi Nlson method). The cultivation was therefore switched over to continuous cultivation. Because the $\mu_{max}$ of the present strain previously measured was 1.2 (1/hr), a sterilized nutrient medium of the aforesaid composition was continuously fed at a rate of 24.0 liters/hr by means of a metering pump, and withdrawn from the fermentor at the same rate. In this way, D was set at 1.00 $\mu_{max}$ (Example 1), and continuous cultivation was performed by using the nutrient medium in an amount 5 times the amount of the culture liquor in the fermentor.

Then, D was changed stepwise to 0.90 $\mu_{max}$ [(21.6 liters/hr), Example 2], 0.83 $\mu_{max}$[(20.0 liter/hr), Comparative Example 1], and 0.67 [(16.0 liters/hr) Comparative Example 2], the continuous cultivation was performed by using the nutrient medium in an amount 5 times as large as that of the culture liquor in the fermentor.

The content of acetate kinase in the bacterial cells obtained in the above manner was measured, and the results are shown in Table 1. Table 1 also shows the data obtained by batchwise cultivation (Comparative Example 3). These data were obtained in the batchwise cultivation before switching over to the continuous cultivation.

TABLE 1

|  | Content of Acetate Kinase (U/g dry cells) | Productivity of Cells (g dry cells/ liter/hr) | Productivity of Acetate Kinase (U/liter/hr) |
| --- | --- | --- | --- |
| Comparative Example 3 | 392 | 0.22 | 86.2 |
| Comparative Example 2 | 360 | 0.52 | 187.2 |
| Comparative Example 1 | 390 | 0.65 | 253.5 |
| Example 2 | 395 | 0.70 | 276.5 |
| Example 1 | 468 | 0.78 | 365.0 |

It is seen from the results shown in Table 1 that when D is at least 0.9 $\mu_{max}$, the content of acetate kinase per unit of cells is higher than that obtained by the batchwise process, the cost of purifying the enzyme can be reduced, the productivity of the cells is good, and that the productivity of acetate kinase is increased up to 4.2 times that obtained by the batchwise process, due to a synergistic effect of the aforesaid factors. On the other hand, when D is less than 0.9 $\mu_{max}$, the content of acetate kinase per unit of cells is lower than that obtained by the batchwise process, and the productivity of cells is better than in the batchwise process. However, the cost of extraction and purification is high, and the process is not economical.

EXAMPLES 3 AND 4 AND COMPARATIVE EXAMPLES 4 AND 5

Strain used:
*Bacillus stearothermophilus* NCA 1503 Composition of a nutrient medium:
  Glucose (carbon source): 1.3 g
  Yeast extract (a product of Oriental Yeast Co., Ltd.): 1.0 g
  Peptone (a product of Difco): 0.5 g
  $KH_2PO_4$: 0.5 g
  $Na_2HPO_4 \cdot 12H_2O$: 0.5 g
  $MgSO_4 \cdot 7H_2O$: 0.1 g
  $ZnSO_4 \cdot 7H_2O$: 0.01 g
  $MnSO_4 \cdot 7H_2O$: 0.01 g
  $CuSO_4 \cdot 5H_2O$: 0.01 g
  $CoCl_2 \cdot 6H_2O$: 0.01 g
  Tap water: 1 liter to dissolve the above ingredients
Pre-cultivation Pre-cultivation was carried out in the aforesaid nutrient medium in the same manner as in Example 1.
Main cultivation A 30-liter fermentor was charged with 20 liters of the aforesaid culture medium and sterilized (121° C., 1 kg/cm², 15 minutes). Under conditions of a cultivation temperature at 55°±1° C., a pH of 6.5–7.0 (adjusted with 4N-NaOH), an air flow rate at 20 liters/rain, and a stirring speed at 900 rpm, batchwise cultivation was performed in the same way as in Example 1. In about 2.5 hours after the initiation of cultivation, $OD_{660\ nm}$ reached 1.2 (0.56 g dry cells/liter), and glucose in the culture broth was almost completely consumed and decreased to less than 0.01% by weight. Immediately, continuous cultivation was started. Since the $\mu_{max}$ of the present strain previously measured was 1.4 (1/hr), the aforesaid sterilized nutrient medium was continuously fed at a rate of 28.0 liters/hr, and the culture broth was withdrawn from the fermentor at the same rate, thereby to prescribe D at 1.00 $\mu_{max}$ (Example 3). The continuous cultivation was performed by using the nutrient medium in an amount 5 times as large as the amount of the cultivation liquor in the fermentor. In the same way as in Example 1, D was changed stepwise to 0.90 $\mu_{max}$ with a rate of supply and withdrawal of 25.2 liters/hr (Example 4), and to 0.75 $\mu_{max}$, with a supply and withdrawal rate of 21.0 liters/hr (Comparative Example 4), and continuous cultivation was conducted to produce bacterial cells.

The content of acetate kinase in the cells so obtained was measured, and the results are shown in Table 2. Table 2 also gives data obtained by batchwise cultivation (Comparative Example 5). These data were obtained with regard to the bacterial cells obtained during batchwise cultivation before switching over to continuous cultivation.

TABLE 2

|  | Content of Acetate Kinase (U/g dry cells) | Productivity of Cells (g dry cells/ liter/hr) | Productivity of Acetate Kinase (U/liter/hr) |
| --- | --- | --- | --- |
| Comparative Example 5 | 620 | 0.23 | 142.6 |
| Comparative Example 4 | 589 | 0.54 | 318 |
| Example 4 | 640 | 0.59 | 374 |
| Example 3 | 880 | 0.65 | 572 |

As shown in Table 2, even when the strain was changed, the relation between D and the content of acetate kinase per unit cells remained established. The bacterial cells produced at a D of at least 0.9 $\mu_{max}$ showed a higher content of acetate kinase than those produced using the batchwise process.

EXAMPLES 5 AND 6 AND COMPARATIVE EXAMPLES 6 AND 7

Stain used:

*Bacillus stearothermophilus* NCA 1503 Composition of a nutrient medium: The same as in Example 1 except that 1.2 g of glycerin was used instead of glucose.

Pre-cultivation

Pre-cultivation was performed in the same way as in Example 2 using the aforesaid nutrient medium, except containing glycerin as a carbon source.

Main cultivation

Batchwise cultivation was initiated, in the same manner as in Example 2. After about 3 hours, $OD_{660\ nm}$ reached 0.9 (0.48 g dry cells/liter), and the concentration of glycerin in the culture broth reached less than 0.01% by weight (measured at 170° C. by Gas-Chromatography GC-3BT, 5% polyethylene glycol 2M column, a product of Shimazu Seisakusho). Continuous cultivation was therefore started. As the $\mu_{max}$ of the present strain previously measured using glycerin as a carbon source was 1.1 (1/hr), D was changed stepwise in the same way as in Example 1, to 1.00 $\mu_{max}$, with a rate of supply and withdrawal of 22.0 liters/hr (Example 5), to 0.90 $\mu_{max}$, with a supply and withdrawal rate of 19.8 liters/hr (Example 6), and to 0.75 $\mu_{max}$, with a supply and withdrawal rate of 16.5 liters/hr (Comparative Example 6), and continuous cultivation was performed to obtain bacterial cells.

The contents of acetate kinase so obtained were measured, and the results are shown in Table 3. For comparison, Table 3 also gives data obtained in the batchwise cultivation (Comparative Example 7). These data were obtained with regard to the cells obtained during the batchwise cultivation before switching over to the continuous cultivation.

TABLE 3

|  | Content of Acetate Kinase (U/g dry cells) | Productivity of Cells (g dry cells/ liter/hr) | Productivity of Acetate Kinase (U/liter/hr) |
|---|---|---|---|
| Comparative Example 7 | 415 | 0.16 | 66.4 |
| Comparative Example 6 | 380 | 0.40 | 152 |
| Example 6 | 420 | 0.48 | 200 |
| Example 5 | 760 | 0.53 | 403 |

As is shown in Table 3, even when the carbon source was changed from glucose to glycerin, the relation between the dilution rate D and the content of acetate kinase per unit cells did not change. The bacterial cells obtained by adjusting D to at least 0.9 $\mu_{max}$ showed a higher content of acetate kinase than the cells obtained by the batchwise process. Thus, the wide applicability of the invention was confirmed.

While the invention has been described in detail and with reference to specific embodiments thereof, it will be apparent to one skilled in the art that various changes and modifications can be made therein without departing from the spirit and scope thereof.

What is claimed is:

1. A process for producing acetate kinase, comprising the steps of cultivating a thermophilic bacterium selected from the group consisting of *Bacillus stearothermophilus* ATCC 7953, *Bacillus stearothermophilus* ATCC 8005, *Bacillus stearothermophilus* ATCC 10149, and *Bacillus stearothermophilus* NCA 1503, which has the ability to produce acetate kinase under continuous cultivation conditions at a dilution rate (D) in the range of from at least 0.9 $\mu_{max}$ to 1.0 $\mu_{max}$, wherein D is the dilution rate (1/hr) and $\mu_{max}$ is the maximum specific growth rate of said bacterium to thereby enhance the acetate kinase content of the cells of said thermophilic bacterium, harvesting said cells, and extracting and purifying said acetate kinase.

2. A process for producing acetate kinase as in claim 1, wherein said cultivating step is carried out under aerobic conditions.

3. A process for producing acetate kinase as in claim 2, wherein said aerobic conditions comprise a concentration of dissolved oxygen of at least 0.5 ppm by weight.

4. A process for producing acetate kinase as in claim 1, wherein said cultivating step is carried out at a temperature of from about 40° C. to 75° C.

5. A process for producing acetate kinase as in claim 1, wherein said cultivating step is carried out at a temperature of from 48° C. to 61° C.

6. A process for producing acetate kinase as in claim 1, wherein the pH during said cultivating step is maintained at from about 4.5 to 9.0.

7. A process for producing acetate kinase as in claim 1, wherein the pH is maintained at from 6.8 to 8.0.

8. A process for producing acetate kinase as in claim 1, wherein said bacterium is *Bacillus stearothermophilus* ATCC 7953.

9. A process for producing acetate kinase as in claim 1, wherein said bacterium is *Bacillus stearothermophilus* ATCC 8005.

10. A process for producing acetate kinase as in claim 1, wherein said bacterium is *Bacillus stearothermophilus* ATCC 10149.

11. A process for producing acetate kinase as in claim 1, wherein said bacterium is *Bacillus stearothermophilus* NCA 1503.

* * * * *